United States Patent [19]
Levy

[11] Patent Number: 5,885,082
[45] Date of Patent: *Mar. 23, 1999

[54] DENTAL AND MEDICAL PROCEDURES EMPLOYING LASER RADIATION

[75] Inventor: Guy Levy, Tustin, Calif.

[73] Assignee: Endo Technic International Corporation, Tustin, Calif.

[ * ] Notice: The portion of the term of this patent subsequent to Jun. 4, 2008, has been disclaimed.

[21] Appl. No.: 709,244

[22] Filed: Jun. 3, 1991

Related U.S. Application Data

[63] Continuation-in-part of Ser. No. 299,472, Jan. 18, 1989, Pat. No. 5,020,995, Ser. No. 335,245, Apr. 10, 1989, abandoned, and Ser. No. 351,203, May 15, 1989, Pat. No. 5,194,005.

[30] Foreign Application Priority Data

Dec. 21, 1988 [FR] France ................................... 88-17549

[51] Int. Cl.$^6$ .................................................... A61C 5/00
[52] U.S. Cl. ............................ 433/215; 433/216; 606/15; 606/16
[58] Field of Search ................................ 433/29, 226, 224, 433/215, 216; 606/2, 3, 10, 15, 16; 128/395, 398

[56] References Cited

U.S. PATENT DOCUMENTS 3,769,963  11/1973  Goldman et al. ............................ 606/3
3,821,510  6/1974  Muncheryon ............................ 128/395

OTHER PUBLICATIONS

Myers et al, "In Vivo Caries Removal Utilizing the YAG Laser", J. of the Michigan Dental Assn., pp. 66–69, Feb. 1985.

Nelson et al, "Ablation of Bone and Methacrylate by a Prototype Mid–Infrared Erbium: YAG Laser", *Lasers in Surgery and Medicine,* 8: 494–500 (1988).

*Primary Examiner*—Cary E. O'Connor
*Attorney, Agent, or Firm*—Pillsbury Madison & Sutro

[57] ABSTRACT

Laser radiation having a selected wavelength and in the form of pulses having a selected pulse duration, repetition rate and energy content per pulse, is employed for performing a variety of dental and medical procedures, including cutting of enamel, dentin, cementum, dental root material, bone and metal. Cavities and openings in teeth and bones can be filled with a mixture containing hydroxyapatite and phosphoric acid, mixed together to form a paste, and the resulting mixture, after being introduced into the opening or cavity, can be cured and hardened by application of pulses of defocused laser radiation.

24 Claims, 1 Drawing Sheet

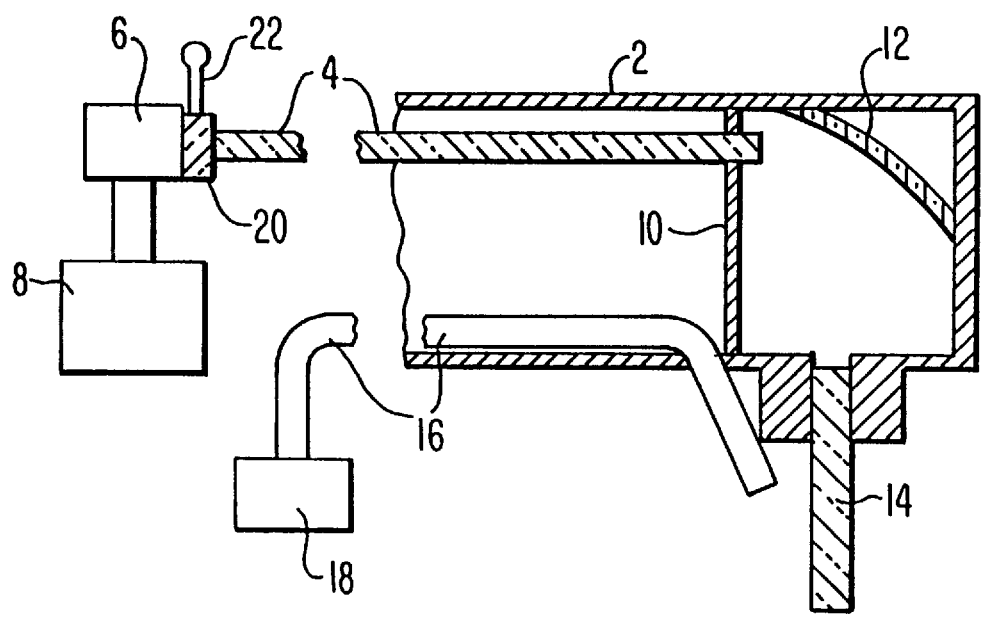

DENTAL AND MEDICAL PROCEDURES EMPLOYING LASER RADIATION

CROSS REFERENCE TO RELATED APPLICATION

This is a continuation-in-part of application Ser. No. 07/299,472, filed on Jan. 18, 1989, now U.S. Pat. No. 5,020,995; application Ser. No. 07/335,245, filed on Apr. 10, 1989, and application Ser. No. 07/351,203, filed on May 15, 1989, now U.S. Pat. No. 5,194,005.

BACKGROUND OF THE INVENTION

The present invention relates to dental and medical procedures employing laser radiation.

In dental procedures, it is frequently desirable to remove portions of tooth enamel, dentin, cementum and root material and in certain cases, portions of gum tissue, in an accurately controlled manner and there has been a growing interest in the use of laser radiation for performing such procedures. In addition, many medical and dental procedures involve removal of bone material. Furthermore, it is desirable to perform all of the above procedures without subjecting the patient to adverse side effects.

The use of laser radiation is attractive because, particularly with the aid of optical fibers, such radiation can be focused to a very small area and is thus compatible with the dimensional scale of dental procedures. Moreover, laser radiation procedures can often be performed without recourse to an anesthetic.

While a number of devices of this type have been proposed, they have not proven to be of practical use notably because even the most effective of those devices already proposed are useful only under limited and very precisely defined conditions.

The enamel and dentin of a tooth include, as one component, hydroxyapatite, which is in amorphous form in the dentin and crystalline form in the enamel. These portions of a tooth additionally include organic tissues and water, but have no vascular system. Healthy dentin is in mineralized form, while dentin which has experienced decay is in demineralized form. Dentin has a relatively high percentage of organic tissue, around 40 percent, and also a high percentage of water. These percentages increase considerably in decayed dentin.

Tooth pulp and the gum surrounding the teeth consist of vascularized organic tissue containing both hemoglobin and water. Each of these components has a different response to laser radiation.

Frequently, when performing medical procedures within the oral cavity, the practitioner encounters metal bodies introduced by previous dental procedures, such bodies being constituted by metal filling material, metal pins, and chrome posts used to secure dental prostheses in place, and it is necessary to cut these bodies, again without producing harmful side effects.

Furthermore, while a number of dental filling materials are presently available, there is a continuing need for material which can fill not only dental cavities, but also cavities existing in, or created in, bone material, and which will have a hardness comparable to that of the natural material which it replaces and form a strong bond with the wall of the cavity or opening.

Application Ser. No. 07/299,472 discloses surgical treatment procedures and instruments for utilizing laser radiation for the removal of tooth and gum tissue.

The inventions disclosed in that application are based on the discovery that laser radiation can be used to cut, by vaporization, both tooth and gum material, as well as other vascularized tissue, with essentially no adverse side effects, if specific parameters and operating conditions are established for the laser radiation.

Specifically various drawbacks associated with earlier proposals could be eliminated, or at least substantially minimized, and an effective cutting action could be achieved, by the use of laser radiation preferably at a wavelength of $1.06\mu$ in the form of pulses having an energy content of between 10 and 50 mJ, with a pulse duration of the order of 100–300 microseconds, and a repetition rate of the order of 50 Hz, and with the radiation beam concentrated at a spot, at the treatment location, of the order of $200–600\mu$.

A pulse duration of $100–300\mu$ sec. has been found to be sufficiently long to avoid subjecting the tissue being treated to thermal shocks but sufficiently short to enable effective control of the heating action to be maintained.

Laser radiation at a wavelength of $1.06\mu$, which can be produced by an Nd YAG laser, can be used for cutting, or vaporizing, demineralized, i.e., decayed, enamel and dentin, without endangering gum tissue. Laser radiation at a wavelength of $532\mu$, which can also be produced by an Nd YAG laser, can also be used, but this requires great care because it has been found that radiation at this wavelength will also cut gum tissue. Therefore, radiation at this wavelength can be used when it is desired to cut gum tissue.

Further, laser radiation at the wavelength of $1.06\mu$ can be made to cut healthy, or mineralized, dentin, and healthy enamel, which was not heretofore considered possible, if a dark colored region is first provided at the spot where cutting is to begin. Specifically, it was found that the absorption of energy at the wavelength of $1.06\mu$ by dark materials is sufficient to enable laser radiation having a suitable energy level to create a plasma which causes vaporization of dentin tissue. It was further discovered that once a plasma cloud capable of vaporizing dentin has been established at a dark colored region, the laser beam can be displaced at a controlled speed from the dark colored region so that the plasma cloud will remain intact and vaporization of healthy dentin will continue.

For cutting dentin and enamel, laser radiation at a wavelength of $1.06\mu$ should be used. Radiation at a wavelength of 0.532 has been found to be effective only if applied at dangerously high energy levels.

Since radiation at $0.532\mu$ can efficiently cut vascularized tissue, it can be used for general surgical procedures. In this case, it was previously disclosed, in application Ser. No. 299,472, that the radiation pulses should have an energy level of not greater than 10 mJ, with a pulse duration of $100–300\mu$ sec., and the radiation could be focussed to a spot $200–600\mu$ in diameter. A pulse repetition rate of the order of 50 Hz could be employed.

The Figure illustrates a handpiece for supplying laser radiation in a form suitable for performing the operations described above. A housing 2 is provided in the form normally utilized for handpieces, which housing would be configured in a manner known in the art for ease of manipulation. The interior of housing 2 is provided with an optical fiber 4 having an input end coupled to a source 6 of monochromatic light, such as an Nd YAG laser producing radiation at a wavelength of $1.06\mu$. Light source 6 is connected to an operating power source 8 which supplies pulses sufficient to cause light source 6 to produce light pulses having the desired parameters.

The free end of fiber 4, in the vicinity of the free end of housing 2, is supported by a suitable support plate 10 to direct light radiation onto a curved mirror 12 which deflects the radiation onto the receiving end of a further optical fiber 14. Mirror 12 additionally performs a focusing action which can focus the radiation emerging from fiber 4 to a point within fiber 14, preferably in the vicinity of the outlet end thereof. This will help to assure that the light emerging from fiber 14 can be concentrated at a sufficiently small spot on the tooth to be treated. Fiber 14 preferably has a very small diameter, possibly of the order of $250\mu$.

Housing 2 additionally contains a hollow tube 16 which is connected to a source 18 of water and/or air and which has an outlet end positioned to direct a stream of the fluid supplied by source 18 into the immediate vicinity of the tooth region to which laser radiation is being applied.

A plate 20 which is capable of influencing the laser radiation so as to double its frequency is slidably mounted on source 6 and is connected to a control handle 22 so as to be slidable, by manipulation of handle 22, between the illustrated position, where plate 20 is interposed in the light path between source 6 and fiber 4, and a retracted position, where plate 20 does not intersect the light path. With this simple arrangement, the handpiece is given the capability of applying either $1.06\mu$ or $0.532\mu$ radiation to the area to be treated, so that only a single laser device need be provided for the selective performance of procedures with radiation of either wavelength.

For performing endodontic treatments within a tooth canal, fiber 14 can be given a suitable length and diameter to be introduced into the canal in order to apply the radiation to the canal walls for widening the canal preparatory to filling.

A dark spot can be formed simply by applying a small amount of graphite, such as used in pencils, with the aid of a small amount of glue. In fact, it has been found possible to achieve the desired result by applying a small quantity of glue to the point of a sharpened pencil and then rubbing the pencil point at the desired location.

For removal of decay, the radiation can have a wavelength of $1.06\mu$ and be in the pulsed form described above.

To dissipate the heat generated by the radiation, water and/or air should be sprayed onto the tooth in the vicinity of the spot which is being irradiated. The rate of flow of fluid depends on the extent to which the fluid absorbs the radiation. For example, water absorbs radiation at $1.06\mu$ at a very low level, but higher than radiation at $0.532\mu$. Therefore, water would be delivered at a higher rate when the latter radiation wavelength is being employed.

When the radiation is applied to demineralized enamel or pathological dentin, a dark spot is not necessary and a plasma forms at the irradiation spot and the affected material is volatilized at and around the spot. The extent of the plasma tends to increase in a short time and this allows for the possibility of reducing the pulse energy to between 10 and 20 mJ.

When cutting normal tissue, the radiation wavelength can be $1.06\mu$, which requires application of a dark spot, and will not affect soft tissues, or $0.532\mu$, which can cut either hard tissues, i.e., dentin and enamel, or soft, vascularized tissues. Each wavelength will be preferable for certain purposes.

Thus, application Ser. No. 299,472 discloses four operating modes responsive to different needs:

1) For cutting demineralized enamel and pathological dentin, use is made of radiation at a wavelength of $1.06\mu$, an energy level of 20–50 mJ, and with the pulse parameters described earlier herein. Labelling with a dark spot is not required.
2) For cutting normal enamel and dentin, the radiation would have the same parameters as for mode 1), but the starting point would be labelled with a dark spot.
3) For cutting any tissue, the same parameters as for mode 1) would be employed, with labelling with a dark spot where possible.
4) For cutting vascularized tissue, including gum and other soft body tissue, laser radiation at a wavelength of $0.532\mu$ would be used, composed of pulses having an energy level of no greater than 10 mJ, without requiring labelling with a dark spot.

For dental treatments, a cooling spray will be used whenever the operation generates a sufficient level of heat.

Application Ser. No. 351,203 discloses further procedures which employ laser radiation for selectively cutting bone, dentin, cementum and dental root material, as well as metal bodies found in the mouth, without exposing the patient to adverse side effects, and particularly burning of tissue adjacent the area being treated. That application additionally discloses procedures for filling cavities or openings in both teeth and bones, using specific filling materials disclosed therein, and to employ laser radiation for promoting hardening of such filling materials.

As disclosed in application Ser. No 351,203, a filling material for teeth is constituted by a mixture formed from a liquid component composed of phosphoric acid and water and a powder component composed of a ceramic and hydroxyapatite, with the ingredients mixed in a proportion to form a paste having a consistency such that the paste is workable and sufficiently self-supporting to be applied to the opening with a spatula and remain in place, and laser radiation having the characteristics to be described below is applied to cure and harden the mixture and bond it to the tooth. The proportions of the mixture are not critical, however, the following are preferred:

Liquid: Phosphoric acid 40%
Water 60%
Powder: Ceramic 80%
Hydroxyapatite 20%

If the proportion of hydroxyapatite is increased, more energy is required to harden the mixture; if it is decreased, the strength of the resulting bond is reduced.

The ceramic component may be composed of corderite, silica or silicium oxide, or aluminum oxide, for example. The powder components will have the grain sizes normally used for dental filling materials.

The liquid and powder components should be mixed together just prior to introduction into the opening to be filled.

The radiation applied during this treatment has a wavelength of $1.06\mu$ and is composed of pulses preferably having a duration of the order of 0.4ms, a repetition rate of the order of 50 Hz and an energy per pulse in the range of 20–100 mJ. However, in contrast to the various cutting operations to be described in detail below, the beam should here be defocused to be at least approximately coextensive with the exposed surface of the filling material. This can easily be achieved by varying the spacing between the radiation output surface of the handpiece and the tooth surface, the area of illumination being readily visible.

The application of radiation to the filling material will promote the growth of a crystal structure in that material and create a strong bond between the hydroxyapatite and the surrounding tooth material.

The radiation will be applied until a crystal structure appears, this generally requiring application of the radiation for a period of 10–30 seconds.

The above described filling material and radiation can be used for filling breaks or gaps in bone material.

Application Ser. No. 351,203 further discloses that it is possible to cut, without burning, bone, root, dentin and cementum in periods of the order of seconds by applying radiation of the type described above together with irrigation with a water/air mixture to control the thermal laser beam cutting action. In this case, the cited application discloses that the radiation wavelength is 1.06$\mu$, the pulse duration is of the order of 0.8–1.2 ms, the pulse repetition rate is in the range of 30–50 Hz and the energy content per pulse is 200–400 mj. At energy levels of this magnitude, cutting can be effected without first forming a dark spot where the radiation is first applied. However, even then application of a dark spot will increase energy absorption and thus speed the cutting operation. In addition, a dark spot can be applied when it is desired to preliminarily mark or outline with a low energy beam the place to be cut.

In addition, radiation having the form described above for cutting bone can further serve to cut metal parts in the mouth, such as metal fillings, pins, or chrome tooth prosthesis posts. For this purpose laser radiation will be created and directed to the material to be cut in the manner described above.

In the performance of all of the cutting operations described above, the light output surface of the handpiece is positioned to focus the radiation to a small spot, preferably having a diameter of the order of 200–600$\mu$.

SUMMARY OF THE INVENTION

It is an object of the present invention to provide alternative approaches to performance of the procedures described above.

A more specific object of the invention is to carry out those procedures utilizing laser radiation pulses having an energy content per pulse different from those disclosed in the earlier applications.

More specifically, compared to the energy levels disclosed in the prior applications, applicant has determined that the cutting of tooth tissue, including particularly enamel, dentin and cementum, as well as bone material, in conjunction with application of a dark spot at the point where cutting is to commence, can be performed with laser radiation pulses having an energy level, or content, per pulse between more than 50 mJ and 100 mJ, particularly if a cooling fluid is delivered to the spot being irradiated with the laser radiation.

For cutting healthy bone, root material, dentin, cementum and enamel without applying a dark coloration to the spot at which cutting is to commence, an energy level per pulse as low as 100 mJ can be employed.

In connection with the filling of openings in tooth material or bone, bonding of the filling composition can be achieved when the applied laser radiation pulses have an energy content between more than 100 mJ and 200 mJ.

For cutting vascularized organic tissue, which includes primarily tooth pulp and gum, with radiation at a wave length of 0.532 micron, the energy per pulse can be as high as 200 mJ if adequate cooling is provided.

To cut metal bodies, the laser radiation can have an energy content of between 50 mJ and less than 200 mJ per pulse, in addition to the range of 200–400 mJ disclosed in application serial number 351,203.

When the practitioner has the possibility of selecting energy levels in the ranges set forth above, in addition to those ranges disclosed in the earlier applications cited herein, wider latitude exists for treating a large variety of conditions. For example, for treating a given condition, the practitioner can select the pulse energy level which will produce the cutting rate which the practitioner prefers to employ. According to another example, the energy level per pulse can be adjusted in accordance with the specific size of the radiation spot on the surface being treated, a larger diameter spot dictating a higher energy level.

BRIEF DESCRIPTION OF THE DRAWING

The sole Figure is a cross-sectional view of a preferred embodiment of an instrument, already described above, which can be employed for performing laser radiation treatments according to the invention.

DESCRIPTION OF THE PREFERRED EMBODIMENTS

The application of laser radiation in all of the procedures to be described herein can be carried out with the apparatus described above and illustrated in the Figure.

Consideration will first be given to procedures for cutting tooth or bone material. The tooth material may include dentin, enamel or cementum, as well as root material. If the material to be cut is capable of having a dark spot applied thereto, cutting can be initiated by applying to the dark spot laser radiation having a comparatively low energy level per pulse.

While prior application Ser. No. 299,472 specifically discloses an energy content per pulse of 10–50 mJ it has been subsequently found that this radiation can also have an energy content per pulse of between greater than 50 mJ and 100 mJ. If the energy content per pulse is higher than 100 mJ, cutting can be initiated without applying a dark spot.

When this procedure is carried out at pulse energy levels of 50–100 mJ, a cooling fluid should be delivered simultaneously to the vicinity of the spot which is being irradiated. In general, the higher the radiation pulse energy level, the greater should be the degree of cooling. As would be apparent, the degree of cooling will depend on the nature of the cooling fluid, i.e., the air-water ratio, the rate of flow of the cooling fluid and the temperature of the cooling fluid. These considerations regarding delivery of cooling fluid are equally applicable to the other procedures to be described below.

For cutting healthy bone, root material, dentin, cementum, and enamel, without applying a dark spot, the energy per pulse can be as low as 100 mJ. When radiation in the range of 100 mJ to 200 mj is employed, the degree of cooling employed can be lower than that required in the case of higher pulse energy levels.

In connection with filing openings in tooth or bone material, the energy level per pulse can be from more than 100 mJ to as high as 200 mJ. The higher energy levels would be employed in those cases where the laser beam is more greatly defocused to cover a larger area. In that case, the higher energy level would create the requisite energy density at the location of the filling material which is to be cured. As an alternative to greater defocusing, the use of pulses having a higher energy level can be accompanied by more intense cooling.

As concerns cutting of vascularized tissue, including gum and pulp, the energy level per pulse can vary between greater than 10 mJ and 200 mJ. The higher energy levels can be employed when the radiation is focused to a relatively large spot size and/or when sufficiently intense cooling is utilized.

For cutting metal bodies in the mouth, energy levels per pulse of between 50 mJ and less than 200 mJ can be employed. These energy levels would be associated with a reduced cooling intensity, compared to cutting at higher energy levels. In all of the procedures described above, cutting operations employing radiation pulses with an energy level in the lower portion of the specified range can be performed more slowly than those employing higher en energy levels per pulse. This may prove desirable in certain cases, either because of the personal preference of the practitioner, particularly if the practitioner does not yet have a great deal of experience with the method, or because this is more appropriate for the particular procedure being performed.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for cutting tooth or bone tissue comprising: imparting a dark coloration to the tissue at a location where the tissue is to be cut; generating laser radiation at a wavelength which is absorbed more strongly by hydroxyapatite than by water; producing a succession of pulses of the generated radiation with an energy level, a pulse duration and repetition rate selected to cut the tissue without causing harmful side effects; concentrating the radiation pulses on the tissue to a spot sufficiently small to cause cutting of the tissue; and supplying a cooling fluid containing water onto the spot simultaneously with said concentrating step.

2. A method as defined in claim 1 wherein the wavelength of the radiation is between 0.5 and 1.1$\mu$.

3. A method as defined in claim 2 wherein the wavelength of the radiation is at least approximately 0.532 or 1.06$\mu$.

4. A method as defined in claim 2 wherein the wavelength of the radiation is 1.06$\mu$.

5. A method as defined in claim 1 wherein said step of concentrating is carried out to limit the radiation to a spot having a diameter not exceeding about 250$\mu$.

6. A method as defined in claim 1 wherein the spot has a diameter of between about 200 and 600$\mu$.

7. A method as defined in claim 1 wherein the pulses have a repetition rate of the order of 50 Hz.

8. A method as defined in claim 1 wherein the pulses have a duration of about 100–300 $\mu$sec.

9. A method as defined in claim 1 wherein the tissue is healthy dentin, enamel, or bone.

10. A method as defined in claim 1 wherein said step of imparting comprises applying a black substance to the tissue.

11. A method as defined in claim 10 wherein the wavelength of the radiation is 1.06$\mu$.

12. A method as defined in claim 1 wherein the cooling fluid contains a mixture of air and water.

13. The method as defined in claim 1 wherein the succession of pulses of the generated radiation have an energy level between more than 50 mJ and 100 mJ per pulse.

14. A method for cutting a material selected from bone, dentin, cementum and dental root material in the body, comprising: generating laser radiation having a wavelength suitable for cutting such material; producing successive pulses of the radiation with an energy level, a pulse duration and repetition rate selected to cut the material without causing harmful side effects; concentrating the radiation pulses on the material to a spot sufficiently small to cause cutting of the material; and, simultaneously with said step of concentrating, directing a cooling fluid containing a mixture of air and water onto the spot.

15. A method as defined in claim 14 wherein the radiation is composed of pulses having a duration of the order of 0.8–1.2 ms, and a repetition rate in the range of 30–50 Hz.

16. A method as defined in claim 14 wherein the successive pulses of the radiation have an energy level between 100 mJ and less than 200 mJ per pulse.

17. A method as defined in claim 14 wherein the successive pulses of the radiation have an energy level between 100 mJ and 400 mJ per pulse.

18. A method as defined in claim 14 wherein the radiation has a wavelength of the order of 1.06$\mu$.

19. A method for removing tooth enamel, comprising the steps of: aiming a pulsed laser so that the output from the laser impinges upon the tooth enamel, repeatedly activating the laser, wherein said laser has an energy output selected to remove the enamel without causing harmful side effects; and supplying a cooling fluid containing water onto the spot simultaneously with impingement of the output of the laser on the tooth enamel.

20. A method as defined in claim 19 wherein the laser output is radiation at a wavelength which is absorbed more strongly by hydroxyapatite than by water.

21. A method as defined in claim 20 wherein the cooling fluid contains a mixture of air and water.

22. A method as defined in claim 19 wherein the cooling fluid contains a mixture of air and water.

23. A method for cutting a material selected from bone, dentin, cementum and dental root material in the body, comprising: generating laser radiation having a wavelength suitable for cutting such material; producing successive pulses of the radiation with an energy level a pulse duration and repetition rate selected to cut the material without causing harmful side effects; concentrating the radiation pulses on the material to a spot sufficiently small to cause cutting of the material; and, simultaneously with said step of concentrating, directing a cooling fluid onto the spot wherein the cooling fluid contains water.

24. A method as defined in claim 23 wherein the successive pulses of the radiation have an energy level between 100 mJ and less than 200 mJ per pulse.

* * * * *